(12) United States Patent
Eggli

(10) Patent No.: US 9,289,285 B2
(45) Date of Patent: *Mar. 22, 2016

(54) DEVICE FOR IMPLANTING A SYSTEM FOR LOADING A CRUCIATE LIGAMENT IN A KNEE JOINT

(71) Applicant: Mathys AG Bettlach, Bettlach (CH)

(72) Inventor: Stefan Eggli, Pierrafortscha (CH)

(73) Assignee: Mathys AG Bettlach, Bettlach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/339,095

(22) Filed: Jul. 23, 2014

(65) Prior Publication Data
US 2014/0336760 A1    Nov. 13, 2014

Related U.S. Application Data

(63) Continuation of application No. 12/810,812, filed as application No. PCT/EP2008/007903 on Sep. 19, 2008, now Pat. No. 8,808,374.

(30) Foreign Application Priority Data

Dec. 27, 2007 (DE) .......................... 10 2007 062 749
Apr. 1, 2008 (DE) .......................... 10 2008 016 607

(51) Int. Cl.
*A61F 2/08* (2006.01)
*A61B 17/04* (2006.01)
*A61B 17/68* (2006.01)

(52) U.S. Cl.
CPC ............ *A61F 2/0811* (2013.01); *A61B 17/0401* (2013.01); *A61B 17/68* (2013.01);
(Continued)

(58) Field of Classification Search
CPC ....... A61F 2/08; A61F 2/0805; A61F 2/0811; A61F 2002/0817; A61F 2002/0823; A61F 2002/0829; A61F 2002/0835; A61F 2002/0841; A61F 2002/0847; A61F 2002/0858; A61F 2002/0864; A61F 2002/087; A61F 2002/0882
USPC ............. 623/13.11–13.14; 606/232, 228, 300
See application file for complete search history.

(56) References Cited

U.S. PATENT DOCUMENTS

| | | | |
|---|---|---|---|
| 4,467,478 A | 8/1984 | Jurgutis | |
| 4,744,793 A | 5/1988 | Parr | |

(Continued)

FOREIGN PATENT DOCUMENTS

| | | | |
|---|---|---|---|
| DE | 3803208 A1 | 10/1989 | |
| DE | 8914308 U1 | 3/1990 | |

(Continued)

OTHER PUBLICATIONS

International Preliminary Report on Patentability, mailed Jun. 27, 2010, issued in corresponding International Application No. PCT/EP2008/007903, filed Sep. 19, 2008, 12 pages.

(Continued)

*Primary Examiner* — Alvin Stewart
(74) *Attorney, Agent, or Firm* — Christensen O'Connor Johnson Kindness PLLC

(57) ABSTRACT

A device for implantation in a bone is disclosed, wherein this device is a component part of a system, for controlled loading of the reconstructure anterior crucual ligament (ACL) of a knee joint. The device may comprise an outer body, which is provided with a damping mechanism between a distal end and a proximal end. Arranged inside the damping mechanism there is at least one securing element for fixing at least one thread which, at the proximal end of the device, is guided out from the outer body through an aperture in the base.

21 Claims, 6 Drawing Sheets

(52) U.S. Cl.
CPC ...... *A61B 17/0487* (2013.01); *A61B 2017/044* (2013.01); *A61B 2017/0448* (2013.01); *A61B 2017/0458* (2013.01); *A61F 2002/0858* (2013.01)

(56) References Cited

U.S. PATENT DOCUMENTS

| | | | |
|---|---|---|---|
| 4,828,562 A | 5/1989 | Kenna | |
| 5,458,601 A | 10/1995 | Young, Jr. | |
| 5,507,812 A | 4/1996 | Moore | |
| 5,702,422 A | 12/1997 | Stone | |
| 6,036,694 A | 3/2000 | Goble | |
| 6,190,411 B1 | 2/2001 | Lo | |
| 7,875,058 B2 | 1/2011 | Holmes, Jr. | |
| 8,110,001 B2 | 2/2012 | Carter | |
| 8,663,325 B2 | 3/2014 | Graf | |
| 8,808,374 B2 * | 8/2014 | Eggli | 623/13.14 |
| 2002/0120349 A1 | 8/2002 | Phillips | |
| 2004/0098050 A1 | 5/2004 | Foerster | |
| 2005/0222488 A1 | 10/2005 | Chang | |
| 2006/0271105 A1 | 11/2006 | Foerster | |

FOREIGN PATENT DOCUMENTS

| | | |
|---|---|---|
| GB | 2 078 528 A | 6/1981 |
| JP | 2000-507469 A | 6/2000 |
| JP | 2006-271429 A | 10/2006 |
| WO | 00/13601 A1 | 3/2000 |
| WO | 02/38059 A2 | 5/2002 |

OTHER PUBLICATIONS

Office Action dated Jun. 24, 2014, issued in corresponding Japanese Application No. 2010540035, filed Jun. 27, 2010, 3 pages.

International Search report, mailed Dec. 19, 2008, issued in corresponding International Application No. PCT/EP2008/007903, filed Sep. 19, 2008.

Office Action dated Feb. 25, 2011, issued in corresponding German Application No. 10 2008 016 607.3, filed Apr. 1, 2008, 54 pages.

* cited by examiner

DEVICE FOR IMPLANTING A SYSTEM FOR LOADING A CRUCIATE LIGAMENT IN A KNEE JOINT

CROSS-REFERENCES TO RELATED APPLICATIONS

This application is a continuation of U.S. patent application Ser. No. 12/810812, filed Sep. 29, 2010, which is the National Stage of International Application No. PCT/EP2008/007903, filed Sep. 19, 2008, all the disclosures of which are incorporated by reference herein.

FIELD OF THE DISCLOSURE

The present disclosure relates to a device for implantation in a bone and to a system for controlled loading of a reconstructed anterior cruciate ligament, wherein the device for implantation according to aspects of the present disclosure is integrated within the system according to aspects of the present disclosure.

BACKGROUND

The human knee joint is stabilized within the interior cavity of the knee joint by the anterior cruciate ligament and the posterior cruciate ligament. In the case of a twisting trauma of the knee joint, these ligaments are very often overstretched until a rupture or tear occurs. In this context, the anterior cruciate ligament is affected approximately nine times more frequently than the posterior cruciate ligament. All attempts at conservative therapy or experiments with stitching the anterior cruciate ligament are associated with considerable problems. Accordingly, in the case of a persistent instability of the injured knee joint, the anterior cruciate ligament is removed according to the prior art, and the stability of the knee joint is restored using a transplant made of tendon material, either of patellar tendon, semitendinous tendon, or quadriceps tendon. One disadvantage of this method is that the latter ligament structure is avital; that is to say, it no longer provides any sensitivity and begins to lose stability again over time.

The published German patent specification DE 38 03 208 A1 describes a device for reconstruction surgery, wherein the anterior cruciate ligament in the human knee joint is permanently restored. In this context, the tibia bone is stabilized relative to the femur, and a full range of movement is restored to the knee by inserting a replacement ligament within the knee joint through precise local attachment of the ends and of the angular position in such a manner that, in the event of a movement of the knee joint, the replacement ligament experiences no change in length (isometric movement) or that the change in length of the replacement ligament corresponds to the physiometric movement of a natural ligament. The disadvantage with this device is that the anterior cruciate ligament in the human knee joint is permanently restored by a replacement ligament, which also comprises a transplant. Accordingly, the injured, natural ligament is permanently removed from the knee joint, and the artificial, replacement ligament takes over its function, only inadequately.

U.S. Pat. No. 5,702,422 describes a method for the repair of tearing and ruptures of an anterior cruciate ligament of a human knee, wherein the ligament is reconnected to its anatomical insertion in the gap between the two condyles of the femur bone by means of a pin for the wound suture. In this context, the healing of the insertion is accelerated by forming a recess in the spongiosa for the collection of blood.

The disadvantage of this method is that the wound suture is connected to the pin, so that a tension is permanently applied to the torn or ruptured ligament, and the healing ligament is longer than the original, healthy ligament and is, accordingly, impaired in its functionality.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Embodiments of the present disclosure relate to a device for implantation in a bone and to a system for controlled loading of a reconstructed anterior cruciate ligament, wherein the device for implantation according to some embodiments of the present disclosure is integrated within the system according to some embodiments of the present disclosure.

Embodiments of the present disclosure are based upon the object, among others, of providing a device and a system for a temporary relief of a reconstructed, natural anterior cruciate ligament in the human knee joint or for any required ligament structure of a human or animal joint.

The device, according to one aspect of the disclosure, for implantation into a bone therefore comprises an outer body, provided with an external screw-thread, which provides a front end and a base. Within its interior, between a distal end and a proximal end, the outer body provides a damping device, wherein at least one fixing element is arranged within the damping device, which fixes at least one thread, which is guided out of the outer body at the proximal end of the device through a recess in the base.

Embodiments of the present disclosure are also based upon the concept that every ligament in the human body provides a largely self-healing tendency. Accordingly, at present, fibulotalar ligament ruptures or AC joint ruptures are practically all treated conservatively. Even a rupture of the large Achilles tendon is nowadays treated conservatively in many centers. As already mentioned, conservative treatment of the anterior cruciate ligament has failed in the past. In fact, scarring of the ligament did occur, but the instability of the knee joint persisted. The stabilizing effect of this ligament is lost, because a knee joint cannot be immobilized for the healing of the ligament structure. The anterior cruciate ligament requires approximately six weeks for primary healing. Immobilization for this duration is absolutely impossible, because the knee joint would become rigid for practical purposes as a result of an immobilization of this kind However, if the knee joint is moved during the healing phase with persistent instability, an antero-posterior translation of the knee joint of up to 10 millimeters occurs with every increasing flexion. This translational instability is, so to speak, built in with the self-healing of the ligament. The ligament cannot heal back to the original length, but is lengthened and therefore no longer fulfills the stabilizing function.

The advantages achieved with the device, according to aspects of the disclosure, for implantation in a bone comprise, in particular, the stabilization of the knee joint during the self-healing phase in every flexional position with exactly the correct antero-posterior translation. In a sense, during the healing phase, the device in accordance with some embodiments, which is conceived as an isotonic knee joint screw and which is an integral component of the system, takes over the joint stabilization, which was formerly provided by the natural, or endogenous and healthy ligament. By means of the isotonic knee joint screw and, respectively, embodiments of the system, with the device, the lower leg is permanently drawn into a posterior drawer position relative to the thigh.

Accordingly, the two ruptured bundles of fibers of the anterior cruciate ligaments are drawn towards one another over a shortest possible distance. With the help of one or more systems disclosed herein, the two ligament stumps can advantageously heal together again in the original position without the loss of stability and with the original length, and, in particular, can therefore once again completely fulfill their original function, the stabilization of the joint.

Furthermore, it is advantageous if the damping device is fitted with a spiral spring, to which a variable pressure can be applied, which can be adjusted in a controlled manner by the operator by means of a tool connected to a force-sensing device. The fact that the spiral spring in some embodiments of the device is arranged on the base of the outer housing, which is formed in a cylindrical shape, advantageously achieves a good mechanical stability in the event of an application of medium to high compressive forces during the implantation.

Furthermore, it is advantageous if the damping device provides an axially displaceable clamping sleeve within the outer body, which moves in the proximal direction in the case of knee bending and knee stretching movements and, in this context, once again compresses the spring so that the knee movements are dampened.

Moreover, it is advantageous if the spiral spring encloses the proximal end of the clamping sleeve and is disposed in contact with the flange of the clamping sleeve. Accordingly, a translational movement of the spiral spring within the interior of the outer body is prevented, since both ends of the spiral spring are mounted on a structurally stable surface.

Moreover, it is advantageous if the flange is provided with an internal screw-thread. As a result of the surface structure of the internal screw-thread, the thread clamped primarily within the flange is subjected to an additional holding.

Furthermore, it is advantageous if the fixing element of some embodiments of the disclosure is designed as a cone. This guarantees that the cone with the wound thread is also accommodated without material stresses within the clamping sleeve, especially within the transitional region towards its flange.

The cone is expediently attached with its distal end to a screw extension of a screw, wherein the screw is to be screwed with its external screw-thread into the internal screw-thread of the clamping sleeve so that the thread can advantageously be wound onto the cone in a controlled manner and can, at the same time, be clamped. Moreover, the advantage is also achieved that the force with which the screw is screwed in is disposed in a defined relationship to the clamping force on the thread, wherein this relationship is naturally known to the user or, respectively, the operator.

According to an advantageous development, the screw head of the screw provides a recess that is formed in the shape of a polygon or, respectively, a hexagon, thereby preventing a slipping of the tool during the application of a tensile force.

In an expedient further development, the thread of the device, according to some embodiments, comprises an elastic material, thereby allowing a uniform tensile stress and preventing a tearing of the thread. In order to reinforce these properties, an additional element is provided in one representative embodiment at the distal end of the elastic thread, wherein this elastic body preferably comprises a polymer or an elastomer. An elastic material for the thread or, respectively, the body, is also advantageous, because the tensile forces on the reconstructed anterior cruciate ligament are relieved and compensated as a result.

Embodiments of the system in accordance with one or more aspects of the disclosure, for a controlled stressing or loading of the reconstructed anterior cruciate ligament during the healing phase advantageously can include an embodiment of the device (isotonic knee joint screw), for implantation in a bone, comprising at least one thread, which is provided as a temporary replacement for the reconstructed anterior cruciate ligament, and a holding element for the at least one thread, with which the tension in the thread is built up.

It is advantageous if the knee joint screw is inserted into a distal bone of a joint in some embodiments, so that the direction of the applied tensile force or, respectively, tensile stress, extends away from the joint. Accordingly, the healing, endogenous anterior cruciate ligament is also advantageously relieved.

Moreover, it is advantageous if the system, according to some embodiments, is based on the device being screwed into the bone at an acute angle relative to the surface of the bone, thereby guaranteeing its stable anchoring, which is not destabilized by a loading with tensile forces. The direction of the acute angle within the bone corresponds largely to the course of the anterior cruciate ligament in the interior of the knee joint.

Moreover, it is advantageous that, after a fitting of the system according to some embodiments, the knee joint remains fixed during the healing phase in the posterior drawer position, and any impacts occurring during daily mobilization exercises or uncontrolled movements during sleep are taken up by the spiral spring.

A further advantage is that the operative intervention for the fitting of the system, according to some embodiments, is implemented in a minimally invasive manner, and only two conventional arthroscopic incisions are required for this purpose.

Furthermore, it is advantageous that the endogenous ligament remains preserved and need no longer be removed. Accordingly, proprioceptivity is also preserved so that the ligament structure is no longer avital after the healing process. Moreover, a removal of exogenous transplant material is no longer required so that the duration of the operative intervention is advantageously practically halved, and the probability of a complication is significantly reduced. Accordingly, once again, the hospitalization of the patient provided with the system, according to some embodiments, is also significantly shortened.

Representative embodiments of the present disclosure are described in the following section. The structure and the use of the examples described herein and its advantages and objects are best understood with reference to the following description in conjunction with the associated drawings.

DESCRIPTION OF THE DRAWINGS

The foregoing aspects and many of the attendant advantages of the present disclosure will become more readily appreciated as the same become better understood by reference to the following detailed description, when taken in conjunction with the accompanying drawings, wherein.

DETAILED DESCRIPTION

Components corresponding to one another are provided with the same reference numbers in all of the drawings.

Figure 1:
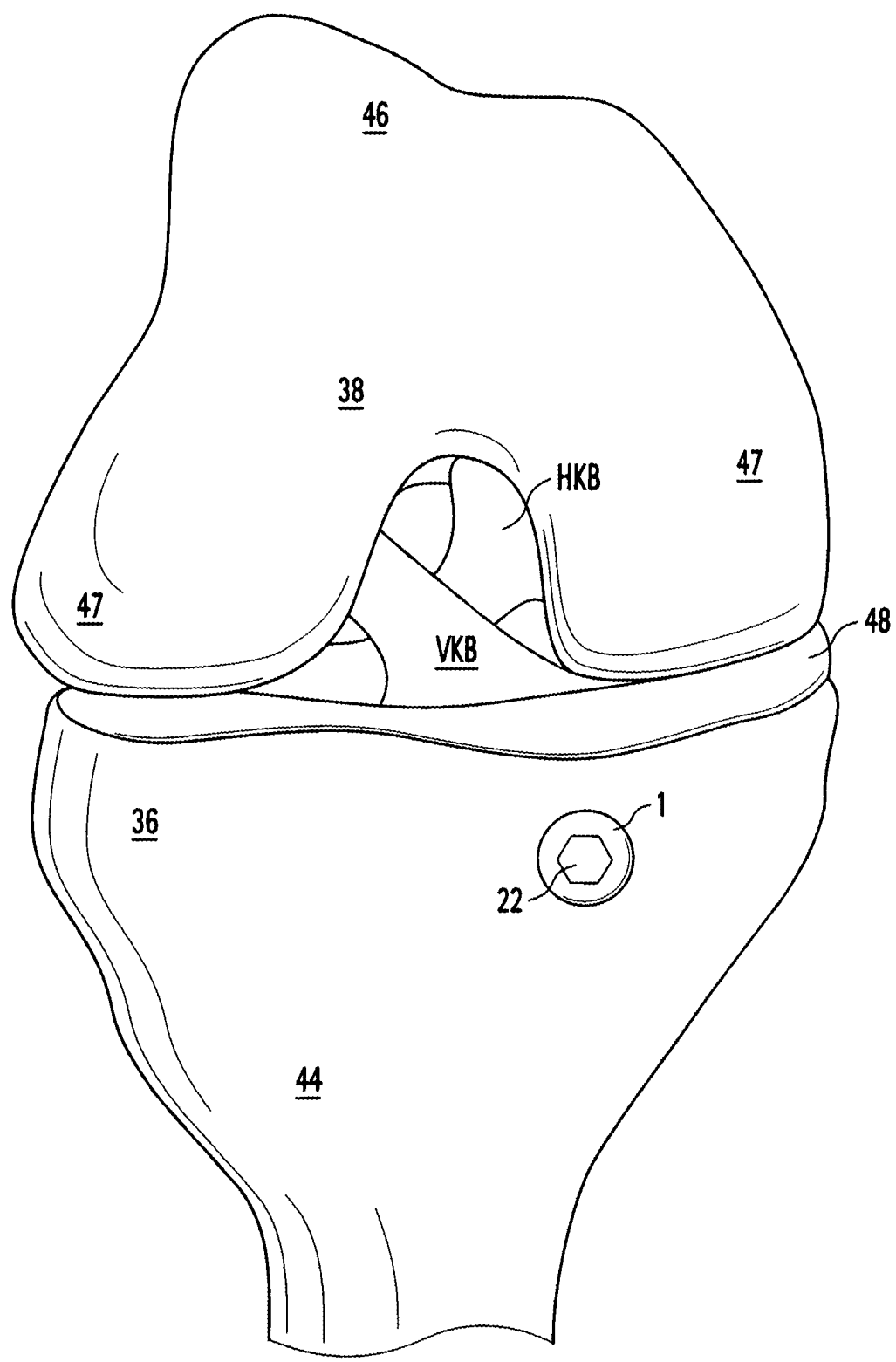
FIG. 1 shows an anterior view of a human knee in the flexed position with a first representative embodiment of the device, according to aspects of the present disclosure.

FIG. 1 shows an anterior view of a human knee joint in the flexed position with a first representative embodiment of the device 1, according to some embodiments of the present disclosure, for implantation in a bone, wherein this representative embodiment of the device 1, according to some embodiments of the present disclosure, comprises a cylindrical outer body 3 provided with an external screw-thread 2 with a front end 4 and a base 5. Within its interior 6, the cylindrical outer body 3 is provided between its distal end 8 and its proximal end 9 with a damping device 7, wherein, within the damping device 7, at least one fixing element 10 is arranged, which fixes at least one thread 11, which is guided at the proximal end 9 of the device 1 through a recess 12 in the base 5 out of the cylindrical outer body 3, which is clearly evident in FIG. 7.

The device 1, according to some embodiments of the present disclosure, can be screwed into a bone at an acute angle α, relative to a tangent to a bone surface into a borehole, which extends in the distal-proximal direction. The acute angle α is disposed within the range from 40° to 50°, but is preferably 45°. This first representative embodiment shows a human knee joint, wherein the device 1, according to some embodiments of the present disclosure, is screwed into a borehole in the proximal end of a tibia bone 44. The position 45 of the borehole is disposed below the anterior cruciate ligament insertion in a lateral-anterior direction.

Figure 2:
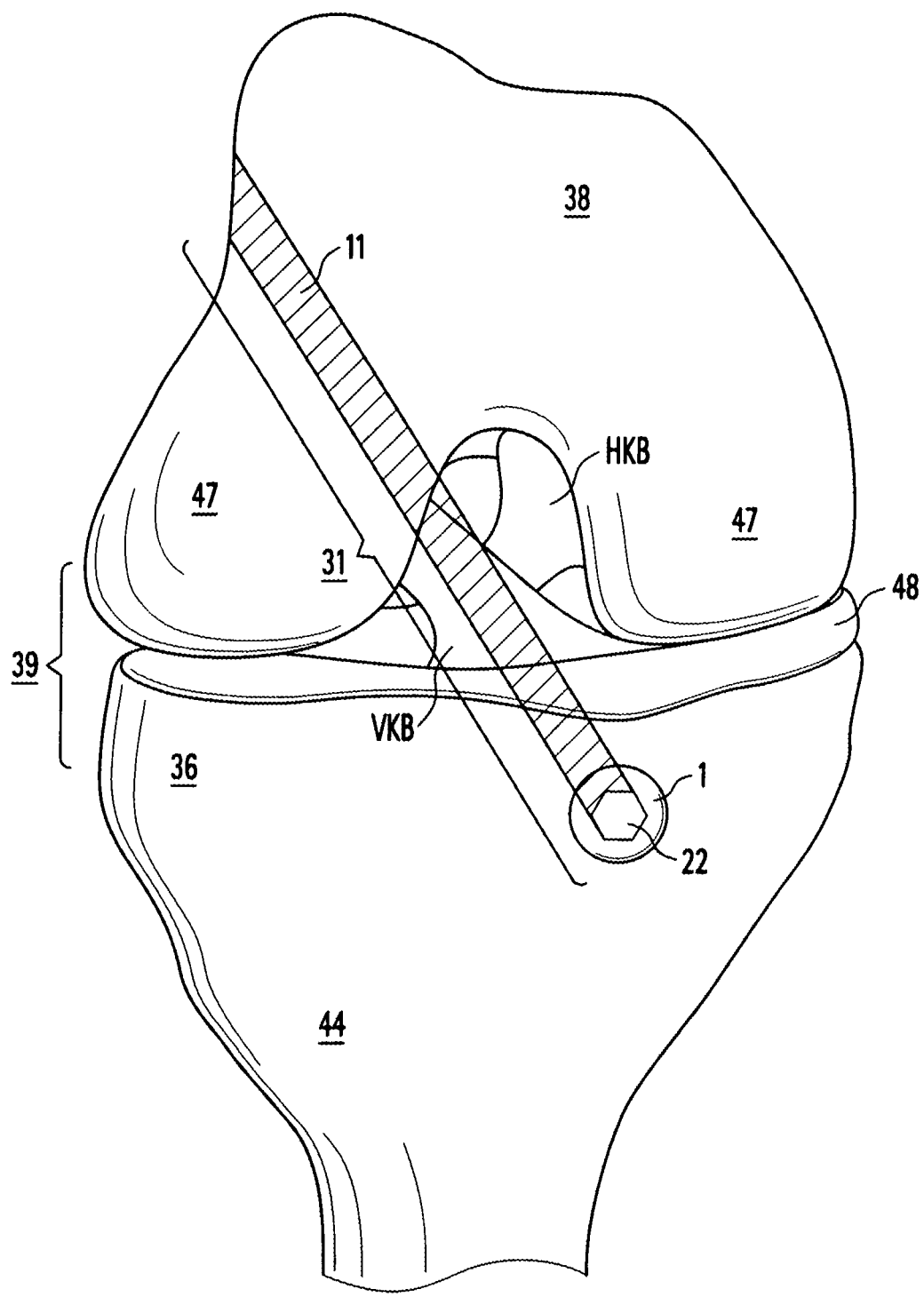
FIG. 2 shows an anterior view of a human knee in the flexed position with a first representative embodiment of the system, according to aspects of the present disclosure, for a controlled loading of an anterior cruciate ligament.

FIG. 2 shows an anterior view of a human knee joint in the flexed position with a representative embodiment of the system, according to some embodiments of the present disclosure, for a controlled stressing or loading of an anterior cruciate ligament ACL. The system 31, according to some embodiments of the present disclosure, for a controlled stressing or loading of the anterior cruciate ligament ACL reconstructed, for example, by stitching, comprises a device 1 for implantation into a bone, at least one thread 11 as a replacement for the reconstructed anterior cruciate ligament ACL and a holding element 32 for the at least one thread 11, and is preferably applied during the healing phase of a ruptured and reconstructed ligament for its relief.

Figure 3A:
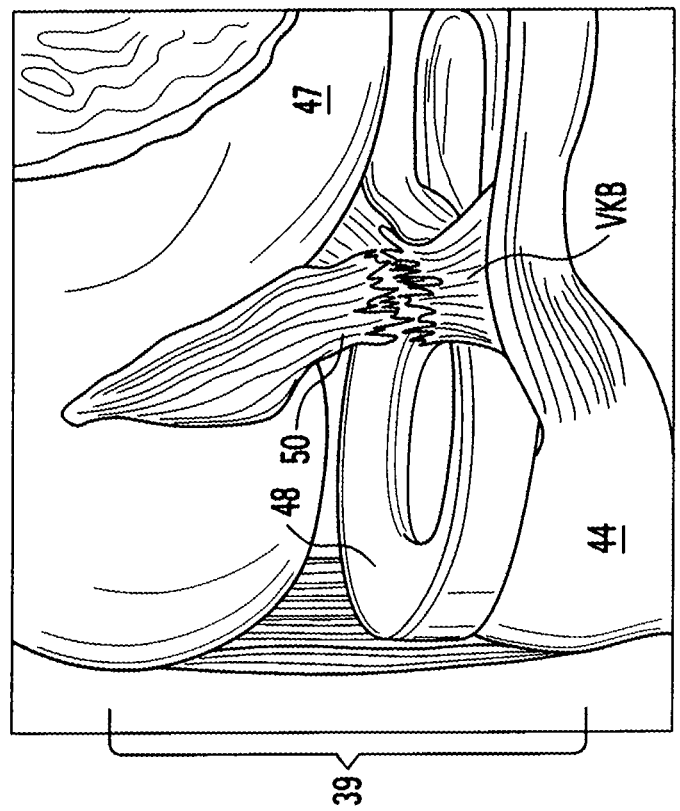
FIG. 3A shows an enlargement of the detail indicated in FIG. 3.
Figure 3:
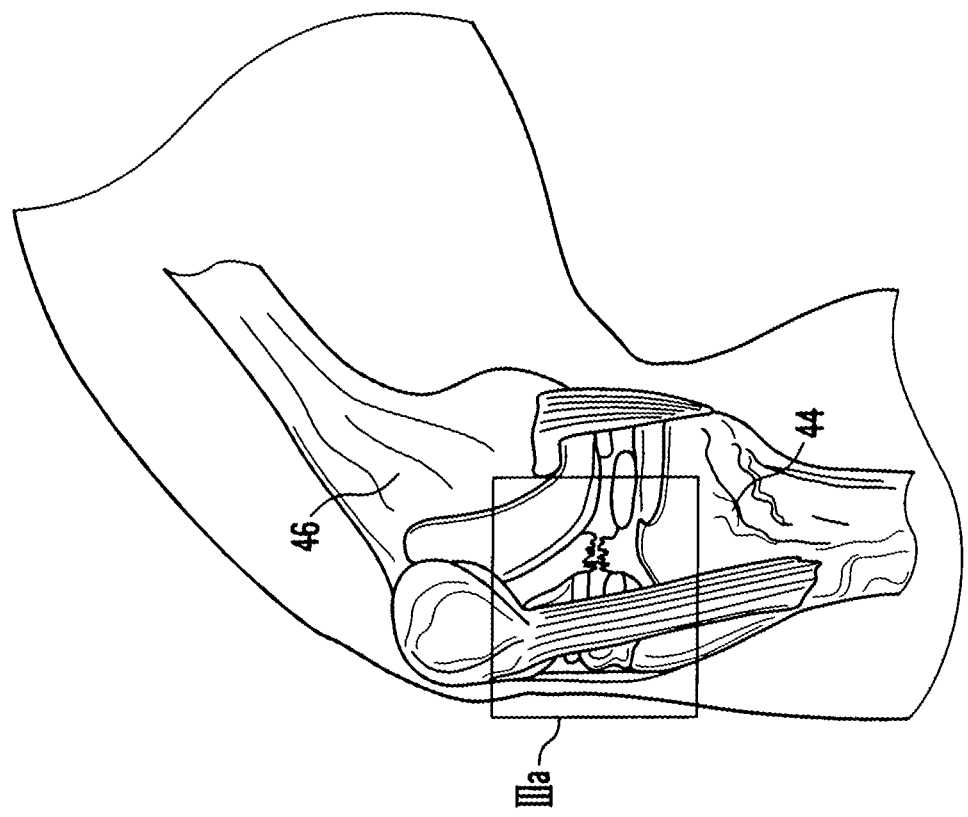
FIG. 3 shows a flexed human knee for which a use of the device, according to aspects of the present disclosure, and the system, according to aspects of the present disclosure, is meaningful.

FIG. 3 illustrates a flexed human knee, for which a use of the device, according to some embodiments of the present disclosure, and of the system, according to some embodiments of the present disclosure, is preferably provided.

FIG. 3A shows an enlargement of the detail indicated in FIG. 3 with an anterior cruciate ligament rupture 50. The ruptured anterior cruciate ligament ACL is reconstructed using appropriate means, wherein, during the subsequent healing phase, the reconstructed anterior cruciate ligament ACL may be stressed only very slightly so that the ruptured anterior cruciate ligament ACL grows together again in such a manner that it can subsequently fulfill its function completely. Because the system 31, according to some embodiments of the present disclosure, providing a device 1 with a damping device 7, comprising a thread 11 and a holding element 32, is used in the injury shown in FIG. 3, the reconstructed anterior cruciate ligament ACL is not stressed even by small movements, since, especially through the at least one thread 11, which is stretched from the tibia to the femur with a defined force of approximately 120 newtons, optimized by the operator, the system 31, according to some embodiments of the present disclosure, completely takes over the function of the healing anterior cruciate ligament ACL.

The device 1, according to some embodiments of the present disclosure, is implanted into a bone 36 at a distal side of a joint. In the case shown in FIGS. 3 and, respectively, 3A, it is the proximal end of a tibia bone 44 that adjoins the human knee joint or, respectively, its joint gap 39.

A variable tensile stress can be applied via the device 1, according to some embodiments of the present disclosure, which is a component of the system 31, also according to some embodiments of the present disclosure, to the at least one thread 11, which takes over the function of the anterior cruciate ligament ACL to be relieved during the healing process so that, during an implementation of the system 31, according to some embodiments of the present disclosure, the operator can adapt the tensile stress in an optimal manner after the reconstruction of the anterior cruciate ligament ACL or, respectively, after the reconstruction of a ligament in general. This guarantees that the system 31, according to some embodiments of the present disclosure, takes over the function of the reconstructed ligament or, respectively, the function of the reconstructed anterior cruciate ligament ACL during its healing phase.

Figure 4:
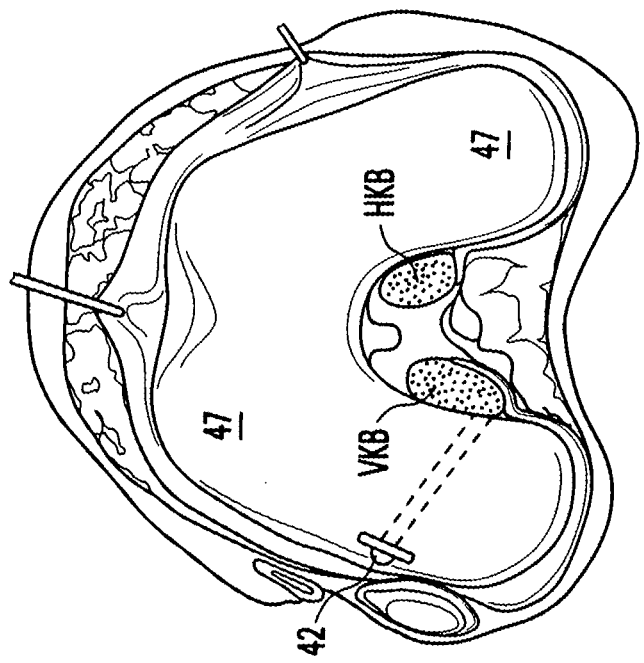
FIG. 4 shows a sectional view of the distal end of a femur bone in the flexed position with the anterior cruciate ligament and the posterior cruciate ligament and the course of at least one thread of the system, according to aspects of the present disclosure, within the medial (internal) condyle.

FIG. 4 shows a sectional view of the distal end of a femur bone 46 or, respectively, a sectional view of both condyles 47 of the human knee joint in the flexed position. The anterior cruciate ligament ACL and the posterior cruciate ligament PCL grow on the inside of the two condyles 47. Furthermore, the system 31, according to some embodiments of the present disclosure, with the holding element 32 and the at least one thread 11 is illustrated schematically in FIG. 4, wherein the holding element 32 and the thread 11, which is indicated by a dotted line, are projected into the plane of the drawing. Within the human knee joint, the at least one thread 11 extends through a first bone tunnel 35 within the tibia bone 44 via the joint gap 39 into a second bone tunnel 37 within a condyle 47, wherein the outlet opening of the second bone tunnel 37 is disposed laterally or, respectively, on the outside of this condyle 47, and the at least one thread 11 is stretched largely parallel to the reconstructed anterior cruciate ligament ACL.

Figure 5:
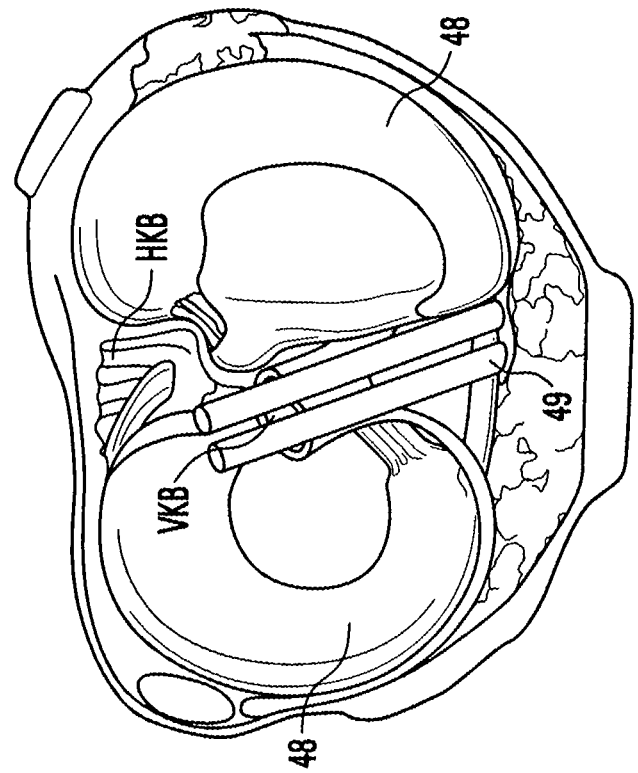
FIG. 5 shows a plan view of a knee joint gap with the two meniscuses and the anterior cruciate ligament and the posterior cruciate ligament.

FIG. 5 shows a sectional plan view of a knee joint gap 39 with the two meniscuses 48 and with the anterior cruciate ligament ACL and the posterior cruciate ligament PCL viewed from proximal or, respectively, from above. With this representative embodiment of the present disclosure, a double thread 49 extends parallel to the anterior cruciate ligament ACL for the relief of the reconstructed anterior cruciate ligament ACL disposed beneath it.

Figure 6:
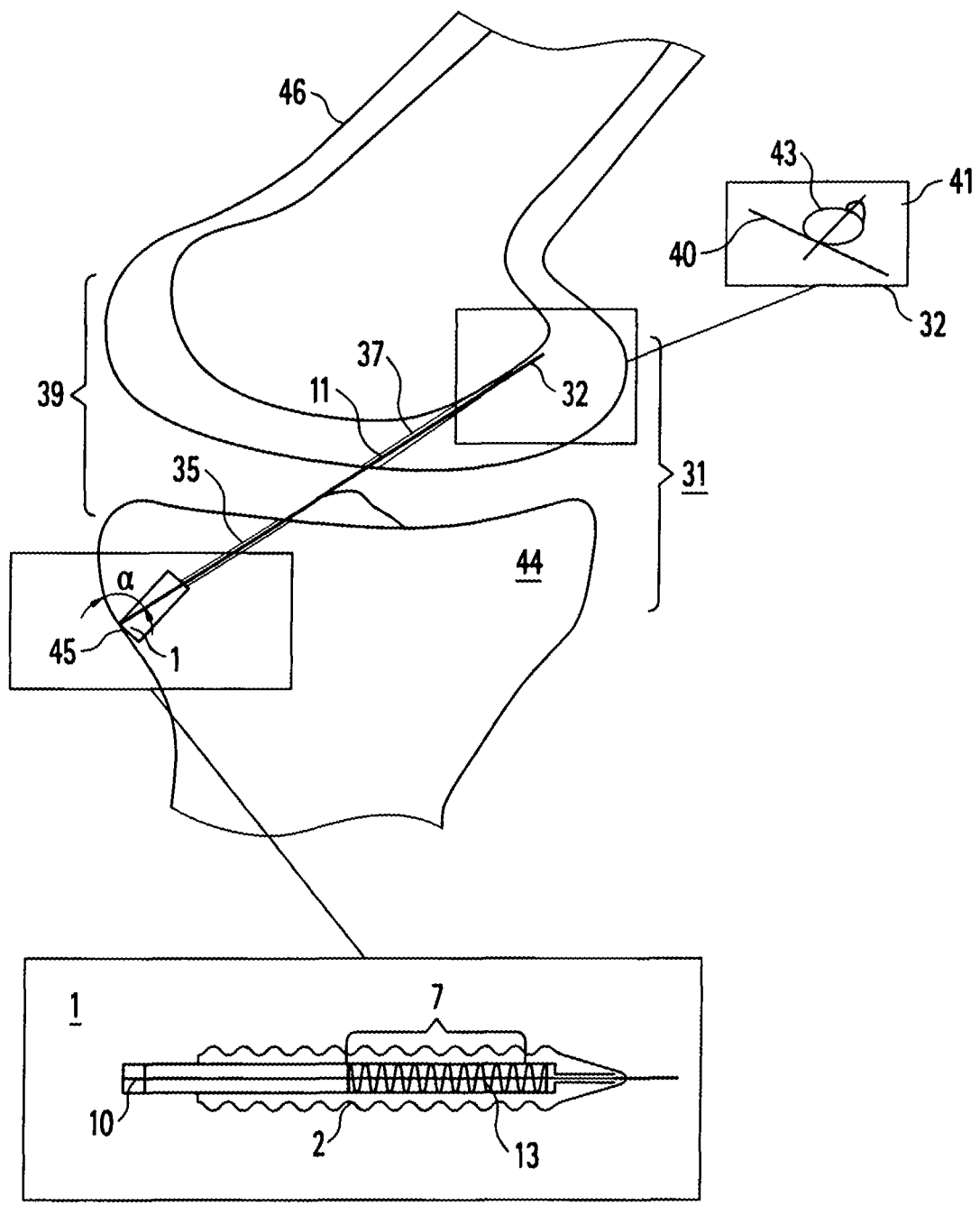
FIG. 6 shows a schematic section disposed parallel to the sagittal plane through a human knee joint, in which the system, according to aspects of the present disclosure, is used.

FIG. 6 shows a schematic section through a human knee joint, disposed parallel to the sagittal plane and held in an isotonic manner in an anterior drawer position, on which the system 31, according to some embodiments of the present disclosure, which comprises a holding element 32, at least one thread 11, and the device 1, according to some embodiments of the present disclosure, is used. In this representative embodiment, the system 31, according to some embodiments of the present disclosure, comprises the device 1 already described for implantation in a bone, preferably in the proximal end of a human tibia bone 44, providing at least one thread 11 as a functional replacement or, respectively, support for the reconstructed ligament or, respectively, the anterior cruciate ligament ACL of a human knee joint, and providing a holding element 32 that attaches the at least one thread 11 to a surface of a proximal bone of a joint, especially of a knee joint during the healing phase of the reconstructed ligament. FIG. 6 shows that the at least one thread 11 extends within a first bone tunnel 35 in a distal bone 36 of a joint, especially of a knee joint, and within a second bone tunnel 37 within a proximal bone 38 of the joint or, respectively, of the knee joint, wherein the thread 11 or, respectively, several threads 49 arranged parallel to one another are stretched across the joint gap or, respectively, across the knee joint gap 39. The at least one thread 11 emerges from the second bone tunnel 38 and is fixed by means of the holding element 32 at a proximal end outside the second bone tunnel 37. The holding element comprises a metal plate 40 and a stopper 41 and is disposed at the proximal end of the second bone tunnel 37, wherein the stopper 41 which is formed as a knot 42 in the thread 11 or, respectively, as a common knot of all threads 49, fixes the thread 11 or, respectively, the threads 49 to the metal plate 40. The stopper 41 can also be formed as a bead 43, wherein the end of the at least one thread 11 is welded to the bead 43 and the bead 43 itself is manufactured from a bio-compatible material.

Figure 7:
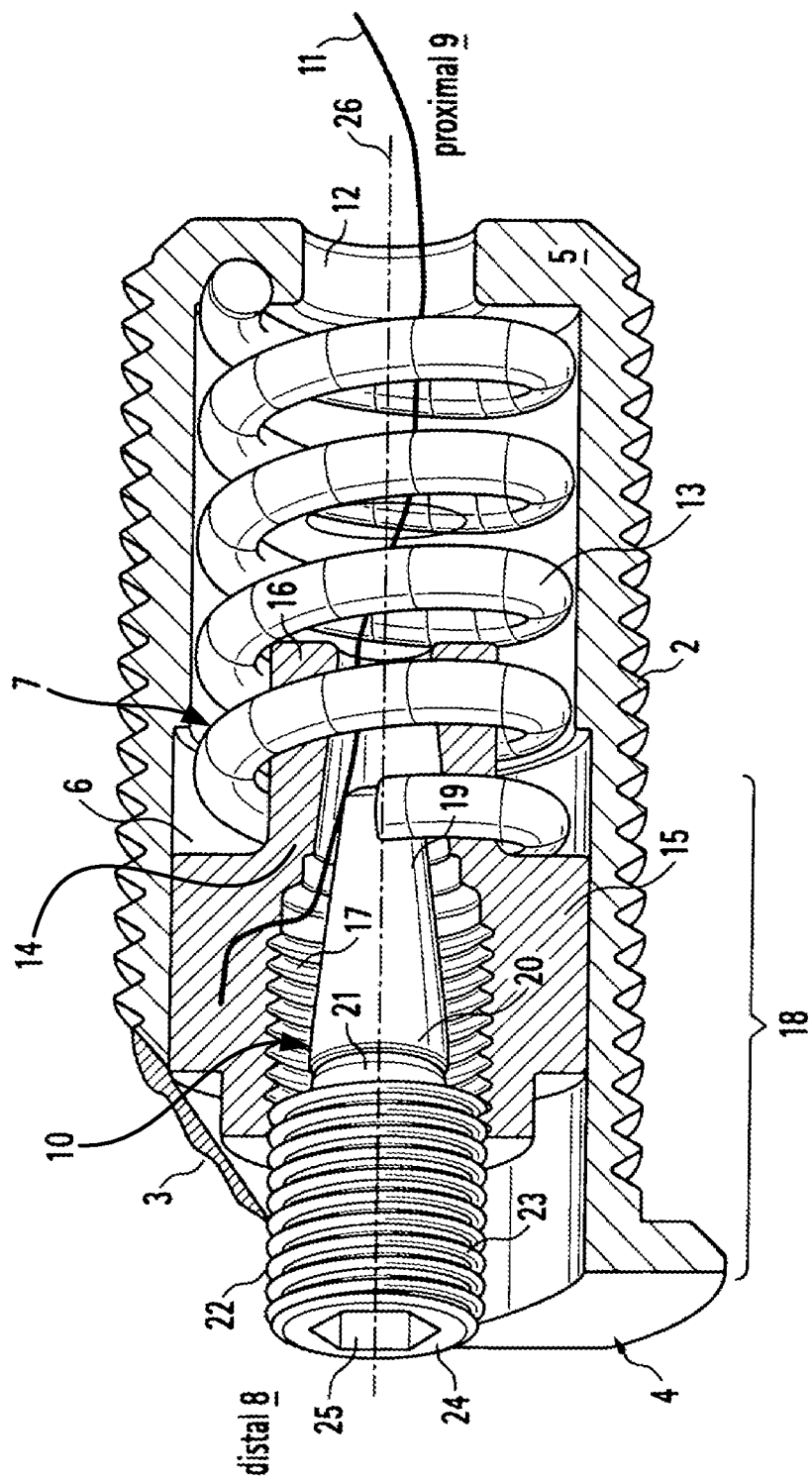
FIG. 7 shows a sectional view of the device, according to aspects of the present disclosure, for implantation in a bone.

FIG. 7 shows a sectional view of the device 1, according to some embodiments of the present disclosure, for implantation in a bone. The device 1, according to some embodiments of the present disclosure, comprises a cylindrical outer body 3 that is provided with an external screw-thread 2 in order to be screwed into a bone 44 or, respectively, into bone tissue. In this manner, the cylindrical outer body anchors itself in the bone tissue in that the latter grows well, especially at the surface of its external screw-thread. The cylindrical outer body 3 provides a front end 4 and a base 5, wherein, after the introduction of the device 1, according to some embodiments of the present disclosure, into the bone, the front end 4 is orientated towards the bone surface. In the interior 6 of the device 1, according to some embodiments of the present disclosure, or, respectively, of the cylindrical outer body 3, a damping device 7 is disposed between a distal end 8 and a proximal end 9, wherein the damping device 7 provides at least one fixing element 10, which is preferably designed as a cone 19 and, at the distal end 8, fixes at least one thread 11, which extends largely within a damping device 7, parallel to its longitudinal axis 26 and is guided out of the cylindrical outer body 3 through a recess 12 in the base 5 at the proximal end 9 of the device 1.

The damping device 7 is fitted with a spiral spring 13, to which a pressure adjustable by an operator is applied, and is in contact at its proximal end 9 with the base 5 of the cylindrical outer body 3. Furthermore, within the damping device 7, a sleeve or, respectively, a clamping sleeve 14 is disposed that provides a flange 15 with an internal screw-thread 17, with which the spiral spring 13 is in contact with its distal end 8. The proximal end 16 of the sleeve 14 is inserted into the spiral spring 13 so that the latter encloses the sleeve 14 in the region of the distal half 18 of the cylindrical outer body 3. The fixing element 10 or, respectively, the cone 19 is attached with its distal end 20 to a screw extension 21 of a screw 22, wherein the screw 22 is provided for a controlled winding of the thread 11 onto the cone 19, thereby increasing the tension of the thread. In this context, the screw 22, of which the screw head 24 provides a recess 25 in the shape of a polygon, preferably a hexagon, is screwed with its external screw-thread 23 into the internal screw-thread 17 of the flange 15.

A further representative embodiment of the device 1, according to some embodiments of the present disclosure, is realized by providing the damping device 7 with a thread 11 made of an elastic material, wherein the thread is attached by clamping to the at least one fixing element 10. The clamping of the elastic thread 11 is realized by winding the latter onto the cone 19 and, accordingly, clamping it to the internal wall at the proximal end 16 of the clamping sleeve 14 and the cone 19.

An additional representative embodiment of the present disclosure is provided by a device 1, according to some embodiments of the present disclosure, with a damping device 7 and an elastic thread 11 at the distal end of which an elastic body comprising a polymer or an elastomer encloses the at least one thread or several threads. However, the two last-named representative embodiments are not illustrated in drawings.

The present disclosure is not restricted to the representative embodiment presented in the drawings, especially not to a use for a knee joint. A use of the present disclosure as a temporary functional replacement for a shoulder joint or another joint is also possible.

It will be appreciated that various changes can be made therein without departing from the spirit and scope of the present disclosure as claimed.

The embodiments of the present disclosure in which an exclusive property or privilege is claimed are defined as follows:

1. A device for implantation into a bone, comprising:
    an outer body provided with an external screw-thread, with a front end and a base;
    a damping device disposed in the interior of the outer body between a distal end and a proximal end, wherein the damping device includes an axially displaceable clamping sleeve disposed within the outer body and a spiral spring, wherein a proximal end of the clamping sleeve is inserted into the spiral spring, wherein the clamping sleeve includes a flange;
    at least one fixing element disposed within the damping device, the at least one fixing element configured to fix at least one thread, which is guided out of the outer body at the proximal end of the device through a recess in the base, wherein the thread is clamped to the at least one fixing element, and
    wherein the clamping sleeve is provided with an internal screw-thread extending from a distal end of the clamping sleeve for threading engagement with a screw over the entire length of the clamping sleeve excluding the proximal end of the clamping sleeve inserted into the spiral spring,
    wherein the flange is provided with at least a portion of the internal screw-thread,
    wherein the screw is to be screwed with its external screw-thread into the internal screw-thread of the flange of the clamping sleeve, and
    wherein a screw head of the screw provides a recess in the form of a polygon or hexagon.

2. The device according to claim 1,
wherein the spiral spring is in contact with the base of the outer body at its proximal end and opposes an applied variable pressure.

3. The device according to claim 1,
wherein the spiral spring is in contact with the flange.

4. The device according to Claim 1,
wherein the clamping sleeve is arranged with its flange in the region of the distal half of the outer body.

5. The device according to Claim 1,
wherein the length of the cone corresponds approximately to the length of the internal screw-thread of the flange.

6. The device according to claim 1,
wherein the fixing element is configured as a cone for accommodation within at least the proximal end of the clamping sleeve, the cone being attached at its distal end to a screw extension of a screw.

7. The device according to claim 1,
wherein an elastic body, which encloses at least one thread or several threads, is provided on the thread at its distal end.

8. The device according to claim 7,
wherein the elastic body is a polymer or an elastomer.

9. The device according to claim 1,
wherein the device can be screwed into a borehole in a bone at an acute angle within the range from 40° to 50° relative to a tangent to a bone surface.

10. The device according to claim 1,
wherein the outer body is cylindrical in shape.

11. A system for a controlled loading of the anterior cruciate ligament (ACL) reconstructed from the two fiber bundles during the healing phase, which provides a device for implantation into a bone according to claim 1, fixes at least one thread as a replacement for the reconstructed anterior cruciate ligament (ACL), and provides a holding element for the at least one thread.

12. The system according to claim 11,
wherein the device can be screwed into a borehole in a bone at an acute angle ($\alpha$) within the range from 40° to 50° relative to a tangent to a bone surface.

13. The system according to claim 11,
wherein a variable tensile stress can be applied via the device to the at least one thread.

14. The system according to claim 11,
wherein the at least one thread extends at one end within a first bone tunnel, wherein the first bone tunnel adjoins the borehole in the distal bone, and also extends within a second bone tunnel in a proximal bone of a joint and bridges a joint gap.

15. The system according to claim 14,
wherein the at least one thread emerges from the second bone tunnel and is fixed by the holding element at a proximal end of the second bone tunnel.

16. The system according to claim 15,
wherein the holding element comprises a metal plate and a stopper, wherein the metal plate is in contact with the proximal end of the second bone tunnel, and the stopper fixes the at least one thread to the metal plate.

17. The system according to claim 16,
wherein the stopper is formed as a knot in the thread or as a common knot of all threads.

18. The system according to claim 17,
wherein the stopper is formed as a bead, wherein one end of the at least one thread is welded or knotted to the bead.

19. The system according to claim 11, wherein the thread is configured to control the loading on the reconstructed anterior cruciate ligament (ACL).

20. The system according to claim 11, wherein the thread coexists with the reconstructed anterior cruciate ligament (ACL) during the healing phase when the device is implanted into a bone at the distal side of a joint.

21. A device for implantation into a bone, comprising:
an outer body provided with an external screw-thread, with a front end and a base;
a damping device disposed in the interior of the outer body between a distal end and a proximal end, wherein the damping device includes an axially displaceable clamping sleeve disposed within the outer body and a spiral spring, wherein a proximal end of the clamping sleeve is inserted into the spiral spring, and wherein the spiral spring is in contact with the base of the outer body at its proximal end and opposes an applied variable pressure;
at least one fixing element disposed within the damping device, the at least one fixing element configured to fix at least one thread, which is guided out of the outer body at the proximal end of the device through a recess in the base, wherein the thread is clamped to the at least one fixing element, and
wherein the clamping sleeve is provided with an internal screw-thread extending from a distal end of the clamping sleeve for threading engagement with a screw over the entire length of the clamping sleeve excluding the proximal end of the clamping sleeve inserted into the spiral spring,
wherein the at least one thread extends within the spiral spring, parallel to its longitudinal axis.

* * * * *